United States Patent [19]

Gehret

[11] Patent Number: 4,954,484

[45] Date of Patent: Sep. 4, 1990

[54] PARASITICIDES AND INSECTICIDES

[75] Inventor: Jean-Claude Gehret, Aesch, Switzerland

[73] Assignee: Ciba-Geigy Corporation, Ardsley, N.Y.

[21] Appl. No.: 172,616

[22] Filed: Mar. 24, 1988

[30] Foreign Application Priority Data

Mar. 27, 1987 [CH] Switzerland .......................... 1180/87

[51] Int. Cl.$^5$ .................. C07D 493/22; A61K 31/365
[52] U.S. Cl. ...................................... 514/30; 514/450; 536/7.1; 549/264
[58] Field of Search .......................... 536/7.1; 549/264; 514/30, 450

[56] References Cited

U.S. PATENT DOCUMENTS

| | | | |
|---|---|---|---|
| 3,950,360 | 4/1976 | Aoki et al. .................... | 260/343.2 R |
| 4,130,519 | 12/1978 | Roper et al. .................. | 260/23.7 |
| 4,173,571 | 11/1979 | Chabala et al. ................ | 260/343.41 |
| 4,328,335 | 5/1982 | Mrozik ....................... | 536/7.1 |
| 4,346,171 | 8/1982 | Takiguchi et al. .............. | 435/119 |
| 4,581,345 | 4/1986 | Wyvratt, Jr. .................. | 536/7.1 X |
| 4,582,852 | 4/1986 | Gehret ....................... | 514/450 |
| 4,778,809 | 10/1988 | Maienfisch et al. ............. | 514/450 |
| 4,791,134 | 12/1988 | Burckhardt ................... | 514/450 |

FOREIGN PATENT DOCUMENTS

| | | | |
|---|---|---|---|
| 170006 | 2/1986 | European Pat. Off. . | |
| 189159 | 7/1986 | European Pat. Off. . | |
| 285561 | 10/1988 | European Pat. Off. ........... | 549/264 |
| 3519834 | 3/1986 | Fed. Rep. of Germany . | |
| 3532794 | 4/1986 | Fed. Rep. of Germany . | |
| 2166436 | 5/1986 | United Kingdom . | |

Primary Examiner—John W. Rollins
Assistant Examiner—W. Catchpole
Attorney, Agent, or Firm—Edward McC. Roberts

[57] ABSTRACT

Novel compounds of formula

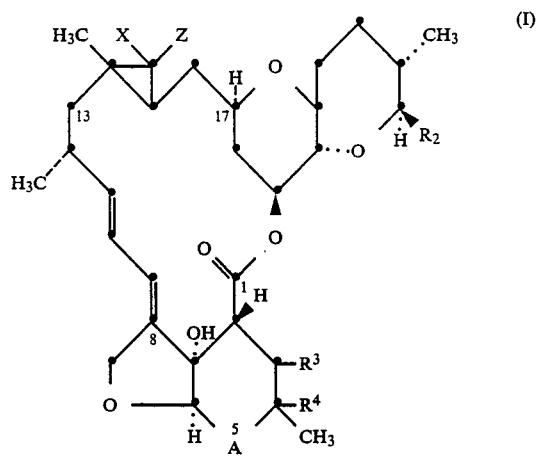

in which
A is a

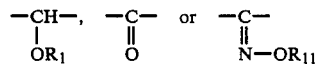

group
wherein $R_1$ is hydrogen or an OH-protecting group, and $R_{11}$ is hydrogen, an OH-protecting group, or an alkyl, cycloalkyl or acyl group,
$R_2$ is methyl, ethyl, isopropyl, sec.-butyl or a —C(CH$_3$)=CH—E group wherein E is methyl, ethyl or isopropyl,
$R_3$ and $R_4$ together represent a bond between the two carbon atoms to which they are bonded, or together represent a —C(X')(Z')— group wherein X' and Z' each represents, independently of the other, hydrogen or halogen, and
X and Z each represents, independently of the other, hydrogen or halogen, the preparation of the novel compounds and the use thereof for controlling parasites of productive livestock and for controlling harmful insects.

13 Claims, No Drawings

PARASITICIDES AND INSECTICIDES

The present invention relates to milbemycin derivatives of formula I

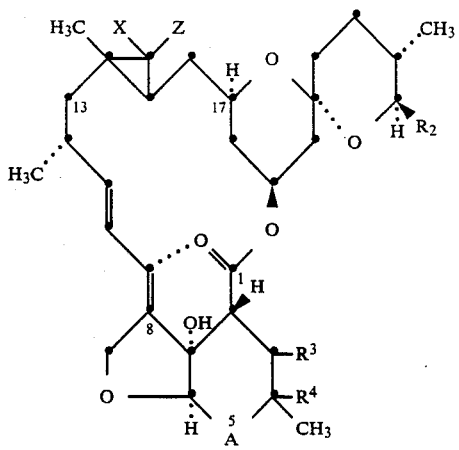

in which

A is a

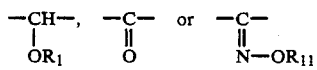

group wherein $R_1$ is hydrogen or an OH-protecting group, and $R_{11}$ is hydrogen, an OH-protecting group, or an alkyl, cycloalkyl or acyl group, $R_2$ is methyl, ethyl, isopropyl, sec.-butyl or a —$C(CH_3)$=CH—E group wherein E is methyl, ethyl or isopropyl, $R_3$ and $R_4$ together represent a bond between the two carbon atoms to which they are bound, or together represent a —$C(X')(Z')$— group wherein $X'$ and $Z'$ each represents, independently of the other, hydrogen or halogen, and X and Z each represents, independently of the other, hydrogen or halogen.

The invention also relates to the preparation of compounds of formula I and to the use thereof for controlling harmful insects or parasites that infest productive livestock, and to compositions that contain at least one of these compounds as active ingredient.

Throughout this specification, compounds in which $R_2$ is sec.-butyl are also to be regarded as milbemycin derivatives although, according to conventional classification, they are derived from avermectin derivatives. Avermectin aglycons (having an OH group in the 13α-position) can, however, be converted into milbemycin homologues in accordance with U.S. Pat. No. 4,173,571.

Naturally occurring milbemycins ($R_1$=H; $R_2$=$CH_3$, $C_2H_5$ or iso-$C_3H_7$) correspond to formula M given below ($C_{14}$-$C_{15}$-double bond):

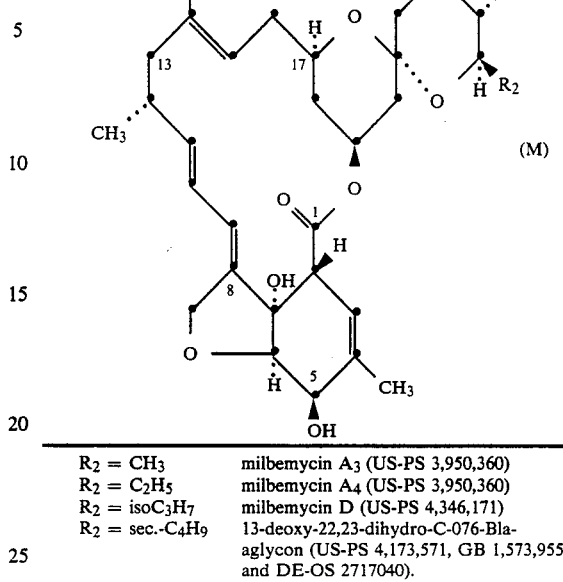

| | |
|---|---|
| $R_2$ = $CH_3$ | milbemycin $A_3$ (US-PS 3,950,360) |
| $R_2$ = $C_2H_5$ | milbemycin $A_4$ (US-PS 3,950,360) |
| $R_2$ = iso$C_3H_7$ | milbemycin D (US-PS 4,346,171) |
| $R_2$ = sec.-$C_4H_9$ | 13-deoxy-22,23-dihydro-C-076-B1a-aglycon (US-PS 4,173,571, GB 1,573,955 and DE-OS 2717040). |

In avermectins, an α-L-oleandrosyl-α-L-oleandrose radical, which is linked via the oxygen atom in α-configuration with the macrolid molecule, is present in the 13-position. Avermectins also differ structurally from milbemycins by a 23-OH group or $\Delta^{22,23}$-double bond and usually by a substituent $R_2$=sec.—$C_4H_9$. By hydrolysing the sugar residue of avermectins it is possible easily to obtain corresponding avermectin aglycons that contain a 13α-hydroxy group adjacent to a C=C double bond. As stated above, avermectin aglycons can be converted into milbemycin homologues. In the milbemycin derivatives of this Application the 22-C atom and the 23-C atom together form the structural moiety —$CH_2$—$CH_2$— as also occurs in formula M.

The constitution of natural antibiotics S541 is known from DE-OS No. 35 32 794 and is as follows:

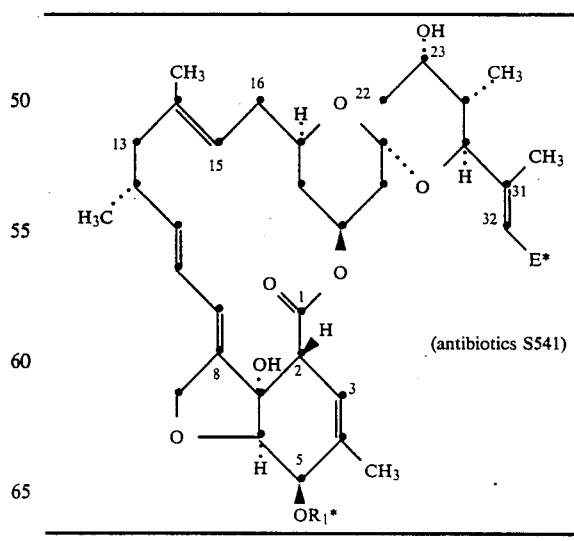

(antibiotics S541)

| | | |
|---|---|---|
| Factor A | E* = iso$C_3H_7$ | $R_1$* = H |
| Factor B | E* = $CH_3$ | $R_1$* = $CH_3$ |

| Factor C | E* = CH₃ | R₁* = H |
| Factor D | E* = C₂H₅ | R₁* = H |
| Factor E | E* = C₂H₅ | R₁* = CH₃ |
| Factor F | E* = isoC₃H₇ | R₁* = CH₃ |

In order to simplify nomenclature, hereinafter the derivatives of antibiotic S541 are classified, according to factor, as derivatives of S541A, S541B, S541C, S541D, S541E or S541F.

Compounds of formula II wherein $R_2$ is a

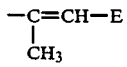

group and E is as defined for formula II, which can be used as starting materials in the process of the invention, can be prepared from the natural antibiotics S541 in a manner known per se.

The hydroxy group in the 23-position in the antibiotics S541 can be removed analogously to the method described in U.S. Pat. No. 4,328,335, and the antibiotics S541 can thus be converted into the corresponding 23-deoxy derivatives. Those compounds having a free 5-OH group ($R^*_1$=H) must first be protected selectively by reaction with one of the silylating reagents Y-Si($R_6$)($R_7$)($R_8$) mentioned below or with tert.-butyl-dimethylsilyloxyacetyl chloride. The reaction of these protected compounds in which $R^*_1$ has been replaced by Si($R_6$)($R_7$)($R_8$) or by C(=O)CH₂OSi—(CH₃)₂tert.-C₄H₉ and the 23-C atom has been substituted by OH, with p-methylphenyl-chlorothionoformate yields derivatives of the antibiotics S541 that are substituted at the 23-position by p—CH₃—C₆H₄—O—C(=S)—O—. These 23-O-(4-methylphenoxy)-thiocarbonyl derivatives of antibiotics S541 are then reduced with tributyl-tin hydride in toluene in the presence of azobisisobutyronitrile at from 80° to 120° C. to form the corresponding 23-deoxy derivatives (23-position unsubstituted).

Compounds of formula I wherein $R_2$ is methyl, ethyl, isopropyl or sec.-butyl are preferred, especially those in which A represents the —CH(OR₁)— and —C(=N—OR₁₁)-groups, and $R_1$ and $R_{11}$ each represents hydrogen.

Throughout this specification, OH-protecting groups for the substituents $R_1$ and/or $R_{11}$ shall be understood as being the protective functional groups conventionally used in organic chemistry. These are especially acyl and silyl groups. Suitable acyl groups are, for example, R₅—C(O)— radicals wherein $R_5$ is C₁-C₁₀-alkyl, C₁-C₁₀-haloalkyl, or a representative of the group comprising phenyl and benzyl which is unsubstituted or is substituted by at least one substituent selected from the group comprising halogen, C₁-C₃-alkyl, C₁-C₃-haloalkyl, C₁-C₃-alkoxy, C₁-C₃-haloalkoxy, cyano and nitro, and is preferably C₁-C₆-alkyl, C₁-C₆-haloalkyl, or phenyl that is unsubstituted or is substituted by halogen, C₁-C₃-alkyl, CF₃ or by nitro. Suitable silyl groups for the radical $R_1$ are the —Si(R₆)(R₇)(R₈) radical wherein $R_6$, $R_7$ and $R_8$, preferably independently of one another, each represents C₁-C₄-alkyl, benzyl or phenyl and, for example, together with the silicon atom form any one of the groups trimethylsilyl, diphenyl-tert.-butylsilyl, bis-(isopropyl)methylsilyl, triphenylsilyl and, especially, tert.-butyldimethylsilyl. The 5-OH group may also the etherified in the form of the benzyl ether or methoxyethoxy methyl ether or, in accordance with published European Patent No. 185,623, may be bonded to a carbohydrate residue, referred to hereinafter as a sugar residue for the sake of simplicity.

In compounds of formula I in which $R_1$ is a silyl group, especially tert.-butyldimethylsilyl, or is an acyl group, for example an R₅—C(O)— group wherein $R_5$ has the meanings given above and is especially methyl, $R_2$, $R_3$, $R_4$, X and Z are preferably as defined in Tables 1 and 2. In compounds of formula I in which $R_{11}$ is a silyl group, especially tert.-butyldimethylsilyl, or is an acyl group, for example an R₅—C(O)-group wherein $R_5$ has the meanings given above and is especially methyl, $R_2$, $R_3$, $R_4$, X and Z are preferably as defined in Tables 5 and 6.

Compounds of formula I wherein $R_1$ and/or $R_{11}$ represent(s) a protecting group can be converted into the highly active free 5-hydroxy derivatives ($R_1$=H) or 5-hydroxyimino derivatives ($R_{11}$=H) by simple removal of the protecting group, for example by hydrolysis, and thus have also the character of intermediates. The biological value of these compounds is not, however, reduced by the protecting group or the sugar residue.

Depending or the number of carbon atoms indicated, the term "alkyl" as a substituent or as part of a substituent shall be understood as meaning, for example, the following groups: methyl, ethyl, propyl, butyl, pentyl, hexyl, heptyl, octyl, nonyl or decyl, and the isomers thereof, such as, for example, isopropyl, isobutyl, tert.-butyl or isopentyl. When $R_{11}$ represents an alkyl group, it contains preferably from 1 to 8, especially from 1 to 4, carbon atoms.

Suitable cycloalkyl groups are mono- to tetra-cyclic groups, such as, for example, cyclopropyl, cyclobutyl, cyclopentyl cyclohexyl, decahydronaphthalene, hydrindane, bicycloheptane, bicyclooctane, norbornane, bornane or adamartyl. These cycloaliphatic groups are preferably unsubstituted or mono- or poly-substituted by methyl. When $R_{11}$ represents a cycloalkyl group, it contains preferably from 3 to 6 carbon atoms.

The above-mentioned acyl and silyl groups serve as protecting groups not only for the hydroxy groups present in the substituent A but also for all other hydroxy groups present in the compounds of the invention or in the precursors of those compounds.

Halogen in the meaning of X, X', Z and Z' is fluorine, chlorine, bromine or iodine, preferably fluorine, chlorine or bromine. Halogen atoms bonded to the same carbon atom are preferably identical with one another. Preferred dihalomethylene groups —C(X)(Z)— and —C(X')(Z')— are dichloromethylene and dibromomethylene.

The following subgroups of compounds of formula I are preferred on account of their pronounced activity against pests: group Ia: compounds of formula I wherein A is any one of the groups —CH(OR₁)—, —C(O)— or —C(=N—OH)— wherein $R_1$ is hydrogen, a silyl group or a monosaccharide group, $R_2$ is methyl or ethyl, $R_3$ and $R_4$ together form a bond between the two carbon atoms to which they are bound, or together form a —C(X')(Z')— group wherein X' and Z' each represents, independently of the other, hydrogen or halogen, and X and Z each represents, independently of the other, hydrogen or halogen;

group Ib: compounds of formula I wherein A is any one of the groups —CH(OR$_1$)—, —C(O)— or —C(=N—OH)— wherein $R_1$ is hydrogen, acetyl, tert.-butyldimethylsilyl or 2,3,4,6-tetraacetylglucopyranosyl, $R_2$ is methyl or ethyl, $R_3$ and $R_4$ together form a bond between the two carbon atoms to which they are bound, or together form a —C(Cl$_2$)— group, X is hydrogen, chlorine, bromine or fluorine, and Z is hydrogen, chlorine, bromine or fluorine, Z preferably being identical with X in compounds in which X is chlorine, bromine or fluorine;

group Ic: compounds of formula I wherein A is any one of the groups —CH(OR$_1$)—, —C(O)— or —C(=N-OH)— wherein $R_1$ is hydrogen, tert.-butyl-dimethylsilyl or 2,3,4,6-tetraacetylglucopyranosyl, $R_2$ is methyl or ethyl, $R_3$ and $R_4$ together form a bond between the two carbon atoms to which they are bound, or together form a —C(Cl$_2$)— group, X is hydrogen, chlorine or bromine, and Z is hydrogen, chlorine or bromine, Z preferably being identical with X in compounds in which X is chlorine or bromine;

group Id: compounds of formula I wherein A is a —CH(OH)— or —C(=N—OH)— group, $R_2$ is methyl or ethyl, $R_3$ and $R_4$ together form a bond between the two carbon atoms to which they are bound, X is hydrogen, chlorine, bromine or fluorine, and Z is hydrogen, chlorine, bromine or fluorine;

group Ie: compounds of formula I wherein A is a —CH(OH)— or —C(=N—OH)— group, $R_2$ is methyl or ethyl, $R_3$ and $R_4$ together form a bond between the two carbon atoms to which they are bound, and X and Z are identical with each other and each represents hydrogen, chlorine or bromine, or X is hydrogen and Z is chlorine or bromine;

group If: compounds of formula I wherein A is a —CH(OH)— group, $R_2$ is methyl or ethyl, $R_3$ and $R_4$ together form a bond between the two carbon atoms to which they are bound, or together form a —CCl$_2$— group, X is hydrogen, chlorine or bromine, and Z is hydrogen, chlorine or bromine.

Within the scope of this application, the structural element

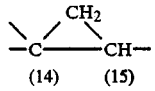

is defined by the term "14,15-dihalomethylene-14,15dihydro";
the structural element

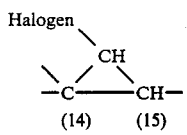

by the term "14,15-methylene-14, 15-dihydro"; the structural element

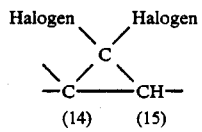

by the term "14,15-monohalomethylene-14,15-dihydro";
the structural element

by the term "5-oxo";
and the structural element

by the term "5-hydroxyamino".

The term used for the optionally halogenated C$_3$–C$_4$-methylene group are analogous to those given for C$_{14}$–C$_{15}$.

Preferred individual compounds are:
5-O-(tert.butyldimethylsilyl)-14,15-dichloromethylene-14,15-dihydromilbemycin A$_4$,
5-O-(tert.butyldimethylsilyl)-3,4-dichloromethylene-14,15-dichloromethylene-3,4,14,15tetrahydromilbemycin A$_4$,
3,4-dichloromethylene-14,15-dichloromethylene-3,4,14,15-tetrahydromilbemycin A$_4$,
5-O-(tert.-butyldimethylsilyl)-14,15-dibromomethylene-14,15-dihydromilbemycin A$_4$,
5-O-(2,3,4,6-tetraacetylglucopyranosyl)-14,15-dichloromethylene-14,15-dihydromilbemycin A$_4$,
5-oxo-14,15-dichloromethylene-14,15-dihydromilbemycin A$_4$,
5-hydroxyimine-14,15-dichloromethylene-14,15-dihydromilbemycin A$_4$,
14,15-dichloromethylene-14,15-dihydromilbemycin A$_3$,
5-O-(tert -butyldimethylsilyl)-14 15-monobromomethylene-14,15-dihydromilbemycin A$_4$,
5-O-(tert.-butyldimethylsilyl)-14,15-methylene-14,15-dihydromilbemycin A$_4$,
14,15-methylene-14,15-dihydromilbemycin A$_4$, and especially
14,15-dibromomethylene-14,15-dihydromilbemycin A$_4$,
14,15-dichloromethylene-14,15-dihydromilbemycin A$_4$,
14,15-monobromomethylene-14,15-dihydromilbemycin A4 and
14,15-monochloromethylene-14 15-dihydromilbemycin A$_4$.

The preparation of compounds of formula I can be effected analogously to those methods described for the addition of carbenes to olefinically unsaturated structures in the literature relating to carbenes, for example in Liebigs Ann. Chem 744, 42–50 (1971) and in Organic Chemistry, Vol. 1, "Carbene Chemistry", W. Kirmse, Academic Press, New York, London, 1971, Part II: "Structure and Reactivity of Carbenes and Carbenoids", especially Chapter 8, including the further reading material cited in the above-mentioned literature.

To prepare compounds of formula I, a compound of formula II

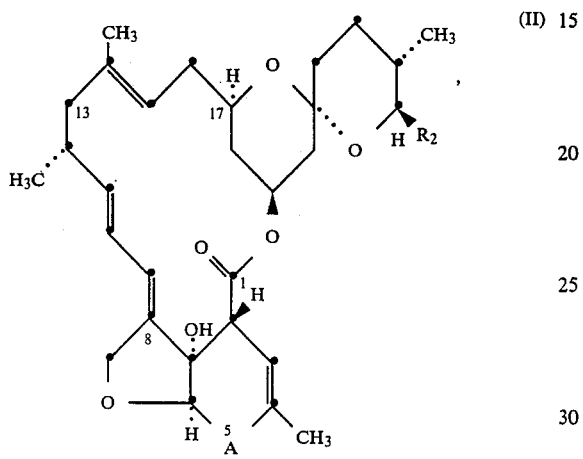

in which A and $R_2$ are as defined for formula I, is reacted with a carbene of formula IIIa $$C(X)(Z) \qquad (IIIa),$$

in which X and Z are as defined for formula I and which is formed in situ and is dissolved in an inert solvent, and, if desired, a resulting compound of formula I in which $R_3$ and $R_4$ together form a bond between the carbon atoms to which they are bound is reacted with a carbene of formula IIIb $$C(X')(Z') \qquad (IIIb),$$

in which X' and Z' are as defined for formula I and which is formed in situ and is dissolved in an inert solvent. Suitable inert solvents are, for example, 1,2-dimethoxyethane, bis(2-methoxyethyl) ether, acetonitrile, dichloromethane, chloroform, dichloroethane and alkanes, such as pentane or hexane. Temperature and reaction time are detered to a large extent by the conditions of the chosen carbene preparation. The temperatures are generally within a range of from −70° C. to +180° C., preferably from 0° C. to 40° C., and the reaction times vary within a range of approximately from 10 minutes to 2 days. Whereas, at low temperatures, compounds of formula I in which $R_3$ and $R_4$ together form a bond between the two carbon atoms to which they are bound (monoadduct) will preferably be formed, at higher temperatures the proportion of compounds in which $R_3$ and $R_4$ together form a —C(X')(Z')— group (diadduct) will predominate.

The manufacture of carbenes of formulae IIIa and IIIb can be effected in conventional manner, such as, for example from a mercury salt, such as, for example, phenyl(trifluoromethyl)-mercury at approximately 80° C.;

from sodium difluorochloroacetate at from 100° C. to 140° C.;

from trichloroacetic acid ethyl ester and a base, such as, for example, sodium methoxide at approximately from 0° C. to 20° C.;

from chloroform or bromoform and a base (for example 30–50% aqueous sodium hydroxide solution, potassium tert.-butoxide or butyllithium) with or without phase-transfer catalysts (such as, for example, tetraalkylammonium chlorides or bromides), at temperatures of approximately from −40° C. to +60° C., chloroform or bromoform simultaneously serving as solvent (yields dihalocarbenes);

from methylene chloride or methylene bromide and a base (for example 30–50% aqueous sodium hydroxide solution, potassium tert.-butoxide or butyllithium) with or without phase-transfer catalysts (such as, for example, tetraalkylammonium chlorides or bromides), at temperatures of approximately from −40° C. to +60° C., it being possible for methylene chloride or methylene bromide to serve simultaneously as solvent (yields monohalocarbenes);

from chloroform, bromoform, methylene chloride or methylene bromide with solid sodium hydroxide or solid potassium hydroxide with exposure to ultrasonic waves.

In compounds of formula I it is possible by reduction to convert mono- and di-halomethylene groups into unsubstituted methylene groups or to convert dihalomethylene groups into monohalomethylene groups. The reduction can be carried out analogously to known methods, for example using tributyltin hydride or zinc and acid.

Compounds of formula I can be obtained, for example, either by converting a milbemycin of formula M or the 23-deoxy derivative of S541A, S541C or S541D into a compound of formula II in which A has a meaning other than —CH((H))— and then reacting with a carbene, or by first reacting a compound of formula M or the 23-deoxy derivative of S541A, S541C or S541D with a carbene and then converting the resulting compound into a compound of formula I in which A has a meaning other than —CH(OH)—.

It is also possible for substituents at the 5-C atom in compounds of formulae I and II to be removed and, if desired, replaced by other substituents provided that these correspond to the definitions according to the invention. The removal and introduction of substituents corresponding to the definitions according to the invention can be carried out by methods that are known per se. In order to introduce acyl, silyl and saccharide groups, it is advantageous to use as starting materials compounds of formulae I and II in which A represents —CH(OH)— or —C(=N—OH)—, or compounds of formula M or the 23-deoxy derivatives of S541A, S541C or S541D. Compounds of formula I or II in which A represents —C(=N—$OR_{11}$)— can be prepared, for example, by reacting compounds of formula I or II in which A represents —C(O)— with hydroxylamine or a salt thereof and, if desired, subsequently introducing the substituent $R_{11}$, which substituent has the meaning given for formula I with the exception of hydrogen, or by carrying out the reaction with a compound of formula $NH_2$-$OR_{11}$ in which $R_{11}$ has the meanings given for formula I with the exception of hydrogen, or with a salt thereof. Suitable salts are, for example, those of the above-mentioned amino compounds with sulphuric acid, nitric acid and, especially, hydrochloric acid. The reaction is advantageously carried out in a suitable solvent, for example a lower alkanol, such as methanol, ethanol, propanol; an ethereal compound, such as tetrahydrofuran or dioxan; an aliphatic carboxylic acid, such as acetic acid or propionic acid; water; or in mixtures of these solvents with each other or with other conventional inert solvents. The reaction temperatures may vary within wide limits. The reaction is advantageously carried out in the range of approximately from $+10°$ to $+100°$ C. If hydroxylamine is employed in the form of ore of its salts, for example in the form of the hydrochloride, in order to bind the acid it is advantageous to add one of the bases customarily used for that purpose and, where appropriate, to carry out the reaction in the presence of a water-binding agent, for example a molecular sieve. Suitable bases are organic and inorganic bases, for example tertiary amines such as trialkylamines (trimethylamine, triethylamine, tripropylamine etc.), pyridine and pyridine bases (4-dimethylaminopyridine, 4-pyrrolidylaminopyridine etc.), oxides, hydrides and hydroxides, carbonates and hydrogen carbonates of alkali metals and alkaline earth metals (CaO, BaO, NaOH, KOH, NaH, $Ca(OH)_2$, $KHCO_3$, $NaHCO_3$, $Ca(HCO_3)_2$, $K_2CO_3$, $Na_2CO_3$), and alkali metal acetates such as $CH_3COONa$ or $CH_3COOK$. Also suitable are alkali metal alcoholates such as $C_2H_5ONa$ n—$C_3H_7ONa$ etc. Triethylamine is preferred.

Compounds of formulae I and II in which A represents —C(O)— can be obtained, for example, by treating compounds of formula I or II in which A represents —CH(OH)— with a reagent suitable for oxidation. Suitable oxidising agents are, for example, activated manganese dioxide, oxalyl chloride/dimethyl sulphoxide/triethylamine or chromium trioxide/pyridine. Another suitable process is the Oppenauer oxidation in which compounds of formulae I and II in which A represents —CH(OH)— are reacted with a ketone, preferable cyclohexanone or acetone, in the presence of an aluminium alcoholate, preferably aluminium isopropoxide or aluminium tert.-butoxide.

The oxidation is advantageously carried out in an inert solvent Suitable solvents are alkanes, such as, for example, hexane, heptane or octane, aromatic hydrocarbons, such as, for example, benzene, toluene or xylenes, or, preferably, chlorinated hydrocarbons, especially methylene chloride. The oxidation is advantageously carried out at temperatures of from $-80°$ C. to $+60°$ C., preferably from $-60°$ C. to $+30°$ C.

From compounds of formulae I and II in which A represents a —C(O)— group it is possible, by reduction in a manner known per se, to obtain again compounds in which A represents a —CHOH— group. The reduction can be effected, for example, by catalytic hydrogenation with a platinum or Raney nickel catalyst or in accordance with the Meerwein-Ponndorf-Verley reduction with aluminium isopropoxide in isopropanol.

The introduction of a saccharide into compounds of formula M, into 23-deoxy derivatives of S541A, S541C or S541D or into compounds of formulae I and II in which A represents —CH(OH)— can be effected by reacting these compounds with the corresponding saccharide, advantageously using methods analogous to those generally known in sugar chemistry for linking reactions, such as, for example, the Koenigs-Knorr method, the Ag-triflate process, the so-called orthoester process, the phenylthio synthesis or the 2-pyridylthio method (in accordance with published European Patent Specification No. 185,623).

For the preparation of compounds of formula II in which $R_1$ is an acyl group, the 5-OH group of a milbemycin of formula M or of a 23-deoxy derivative of S541A, S541C or S541D is acylated. The introduction of the acyl group is usually carried out using the corresponding acyl halides or acyl anhydrides, the term "acyl halide" meaning acyl chloride or acyl bromide, and is preferably used to introduce the $R_5C(O)$— group defined at the beginning.

For the preparation of compounds of formula II in which $R_1$ is a silyl group, the 5-OH group of a milbemycin of formula M or of a 23-deoxy derivative of S541A, S541C or S541D is silylated. For the silylation there is advantageously used a silane of formula Y-$Si(R_6)(R_7)(R_8)$ in which $R_6$, $R_7$ and $R_8$ have the meanings mentioned hereinbefore and Y represents a silyl leaving group. Silyl leaving groups Y include, for example, bromine, chlorine, cyano, azido, acetamide, trifluoroacetcxy and trifluoromethanesulphonyloxy. This list does not constitute any limitation; the skilled person will know other typical silyl leaving groups 5-O-acylations and 5-O-silylations are carried out in anhydrous medium, preferably in inert solvents and, especially, in aprotic solvents. The reaction proceeds advantageously within a temperature range of from $0°$ to $+80°$ C., preferably from $+10°$ to $+40°$ C. It is preferable to add an organic base. Suitable organic bases are, for example, tertiary amines such as triethylamine, triethylenediamine, triazole and preferably pyridine, imidazole or 1,8-diazabicyclo[5.4.0]undec-7-ene (DBU).

The removal of these silyl and acyl radicals $R_1$ or $R_{11}$ in the 5-position is effected by selective mild hydrolysis (→$R_1$ or $R_{11}$=H) for example with dilute acids such as dilute HCl, HF, arylsulphonic acid in alcoholic or aqueous solution, or in accordance with another method familiar to the skilled person. Acyl radicals are preferably removed under basic conditions (for example in alcoholic ammonia solution).

The process of the invention for the preparation of compounds of formula I wherein A, $R_2$, $R_3$, $R_4$, X and Z are as defined for formula I comprises reacting a compound of formula II

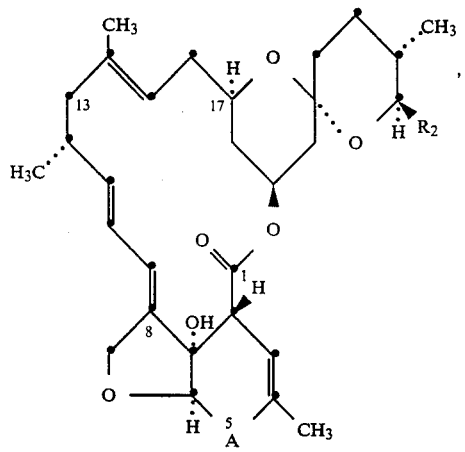

(II)

in which A and R$_2$ are as defined for formula I, with a carbene of formula IIIa $$C(X)(Z) \quad \text{(IIIa)}$$

in which X and Z are as defined for formula I and which is formed in situ and is dissolved in an inert solvent; and, in resulting compounds, if desired (i) reducing a —C(halogen)(halogen)— group that represents —C(X)(Z)— to a —CH(halogen)— or —CH$_2$— group or (ii) reducing a —CH(halogen)— group that represents —C(X)(Z)— to a —CH$_2$— group or (iii) converting the group that represents A into another of the groups defined under A, or reacting resulting compounds in which R$_3$ and R$_4$ together form a bond between the two carbon atoms to which they are bound with a carbene of formula IIIb $$C(X')(Z') \quad \text{(IIIb)}$$

in which X' and Z' are as defined for formula I and which is formed in situ and is dissolved in an inert solvent, and, in resulting compounds, if desired (iv) reducing a —C(halogen)(halogen)— group that represents —C(X)(Z)— or —C(X')(Z')— to a —CH(halogen)— or —CH$_2$group or (v) reducing a —CH(halogen)— group that represents —C(X)(Z)— or —C(X')(Z')— to a —CH$_2$— group or (vi) converting the group that represents A into another of the groups defined under A.

The present invention relates also to the described process for the preparation of compounds of formula I.

The compounds of formula I are eminently suitable for controlling pests of animals and plants, especially ectoparasites of animals. These last-mentioned pests comprise, of the order Acarina, especially pests of the families Ixodidae, Dermanyssidae, Sarcoptidae and Psoroptidae; the orders Mallophaga, Siphonaptera and Anoplura (for example the Haemotopinidae family); and of the order Diptera, especially pests of the families Muscidae, Calliphoridae, Oestridae, Tabanidae, Hippoboscidae and Gastrophilidae.

The compounds I can also be used to control hygiene pests, especially of the order Diptera comprising the families Sarcophagidae, Anophilidae and Culicidae; of the order Orthoptera, of the order Dictyoptera (for example the Blattidae family) and of the order Hymenoptera (for example the Formicidae family).

The compounds I also have lasting action against mites and insects that are parasites of plants. When used to control spider mites of the order Acarina, they are effective against eggs, nymphs and adults of Tetranychidae (Tetranychus spp. and Panonychus spp.).

They have high activity against sucking insects of the order Homoptera, especially against pests of the families Aphididae, Delphacidae, Cicadellidae, Psyllidae, Coccidae, Diaspididae and Eriophydidae (for example the rust mite on citrus fruits); of the orders Hemiptera, Heteroptera and Thysanoptera; and against plant-eating insects of the orders Lepidoptera, Coleoptera, Diptera and Orthoptera.

They are also suitable as soil insecticides against soil pests.

The compounds of formula I are therefore effective against all developmental stages of sucking and feeding insects in crops such as cereals, cotton, rice, maize, soybeans, potatoes, vegetables, fruits, tobacco, hops, citrus fruit, avocados and others.

The compounds of formula I are also effective against plant nematodes of the species Meloidogyne, Heterodera, Pratylenchus, Ditylenchus, Radopholus, Rhizoglyphus and others.

The compounds are also effective against helminths in all developmental stages, and among these the endoparasitic nematodes can be the cause of severe diseases in mammals and fowl, for example sheep, pigs, goats, cattle, horses, donkeys, dogs, cats, guinea pigs, cage birds. Typical nematodes having this indication are: Haemonchus, Trichostrongylus, Ostertagia, Nematodirus, Cooperia, Ascaris, Bunostomum, Oesophagostomum, Chabertia, Trichuris, Strongylus, Trichonema, Dictyvocaulus, Capillaria, Heterakis, Toxocara, Ascaridia, Oxyuris, Ancylostoma, Uncinaria, Toxascaris and Parascaris. The particular advantage of the compounds of formula I is their activity against parasites that are resistant to benzimidazole-based active substances.

Certain species of the genera Nematodirus, Cooperia and Oesophagostomum attack the intestinal tract of the host animal, whereas others of the genera Haemonchus and Ostertagia parasiticise the stomach and those of the genus Dictyocaulus the lung tissue. Parasites of the families Filariidae and Setariidae are found in internal cell tissue and in organs, for example in the heart, blood vessels and lymph vessels and in subcutaneous tissue. In this connection, particular mention should be made of the dog heartworm, Dirofilaria immitis. The compounds of formula I are highly effective against these parasites.

The compounds of formula I are also suitable for controlling pathogenic parasites in humans, among which parasites there may be mentioned as typical representatives occurring in the alimentary tract those of the genera Ancylostoma, Necator, Ascaris, Strongyloides, Trichinella, Capillaria, Trichuris and Enterobius. The compounds of this invention are also effective against parasites of the genera Wuchereria, Brugia, Onchocerca and Loa of the Filariidae family, which occur in the blood, in tissue and various organs, and, in addition, against Dracunculus and parasites of the genera Strongyloides and Trichinella which infest in particular the gastro-intestinal tract.

The compounds of formula I are used in unmodified form, or preferably together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the composition:, the methods of application such as spraying, atomising, dusting, scattering or pouring, are chosen in accordance with the intended objectives and the prevailing circumstances.

The compounds of formula I are administered to warm-blooded animals in amounts of from 0.01 to 10 mg/kg of body weight. Over enclosed crop areas they are applied in amounts of from 10 g to 1000 g per hectare. They are also used in pens, paddocks, stalls and other livestock buildings.

The formulations, i.e. the compositions, preparations or mixtures containing the compound (active ingredient) of formula I are prepared in known manner, e.g. by homogeneously mixing and/or grinding the active ingredients with extenders, such as, e.g. solvents, solid carriers and, where appropriate, surface-active compounds (surfactants).

Suitable solvents are: aromatic hydrocarbons, preferably the fractions containing 8 to 12 carbon atoms, such as, for example, xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, as well as vegetable oils or epoxidised vegetable oils, such as epoxidised coconut oil or soybean oil; or water.

The solid carriers used, for example for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers Suitable granulated adsorptive carriers are porous types, such as, for example, pumice, broken brick, sepiolite or bentonite; and suitable nonsorbent carriers are materials such as calcite or sand. In addition, a great number of pregranulated materials of inorganic or organic nature can be used, such as especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as including mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), such as, for example, the sodium or potassium salts of oleic or stearic acid, or of natural fatty acid mixtures which can be obtained, for example, from coconut oil or tallow oil. Other suitable surfactants are also the fatty acid methyltaurin salts.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammonium salts and contain a ($C_8$–$C_{22}$-alkyl radical, alkyl also including the alkyl moiety, of acyl radicals, for example the sodium or calcium salt of lignosulphonic acid, of dodecylsulphate or of a mixture of fatty alcohol sulphates obtained from natural fatty acids. These compounds also comprise the salts of the sulphuric acid esters and sulphonic acids of fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and formaldehyde.

Also suitable are corresponding phosphates, such as, for example, salts of the phosphoric acid ester of an adduct of p-nonylphenol with 4 to 14 moles of ethylene oxide; or phospholipids.

Non-ionic surfactants are especially polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are especially quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methyl sulphates or ethyl sulphates, e.g. stearyltrimethylammonium chloride or benzyldi-(2-chloroethyl)ethylammonium bromide.

The surfactants customarily employed in the art of formulation are described inter alia in the following publication: "1986 International McCutcheon's Emulsifiers and Detergents", The Manufacturing Confectioner Publishing Co., Glen Rock, N.J., USA.

The pesticidal compositions usually contain from 0.01 to 95%, especially from 0.1 to 80%, of an active ingredient of formula I, from 5 to 99.99% of a solid or liquid adjuvant, and from 0 to 25%, especially from 0.1 to 25%, of a surfactant.

Whereas commercial products are preferably formulated as concentrates, the end user will normally employ dilute formulations having an active ingredient content of from 1 to 10,000 ppm.

The present invention therefore also relates to pesticidal compositions which contain as active ingredient at least one compound of formula I together with customary carriers and/or dispersing agents.

The compositions may also contain further ingredients such as stabilisers, antifoams, viscosity regulators, binders, tackifiers and also fertilisers or other active ingredients for obtaining special effects.

Preparation Examples

Example P-1: Preparation of
5-O-(tert.-butyldimethylsilyl)-14,15-dichloromethylene-14,15-dihydromilbemycin $A_4$ and
5-O-(tert.-butyldimethylsilyl)-3,4-dichloromethylene-14,15-dichloromethylene-3,4,14,15-tetrahydromilbemycin $A_4$ With continuous stirring at from 0 to 5° C., 15 ml of a 50% aqueous sodium hydroxide solution are added to a solution of 1300 mg of 5-O-(tert.-butyldimethylsilyl)milbemycin $A_4$ and 15 mg of tetrabutylammonium chloride in 60 ml of chloroform. After 30 minutes, the reaction mixture is diluted with 200 ml of ethyl acetate and washed until neutral with water/sodium chloride solution. After drying the solution over sodium sulphate and concentrating by evaporation, the residue is purified over silica gel (hexane:ether=5:1). Freeze-drying of the product yields 1090 mg of 5-O-(tert.-butyldimethylsilyl)-14, 15-dichloromethylene-14,15-dihydromilbemycin $A_4$, m.p. 102°–105° C., and 80 mg of 5-O-(tert.-butyldimethylsilyl)-3,4-dichloromethylene-14,15-dichloromethylene-3,4,14,15-tetrahydromilbemycin $A_4$, m.p. approximately 200° C.

By removing the silyl group from 5-O-(tert.-butyldimethylsilyl)-3,4-dichloromethylene-14,15-dichloromethylene-3,4,14,15-tetrahydromilbemycin $A_4$, 3,4-dichloromethylene-14,15-dichloromethylene-3,4,14,15-tetrahydromilbemycin $A_4$, m.p. 153°–157° C., is obtained.

Example P-2: Preparation of
14,15-dichloromethylene-14,15-dihydromilbemycin $A_4$ 120 mg of 5-O-(tert.-butyldimethylsilyl)-14,15-dichloromethylene-14,15-dihydromilbemycin $A_4$ in 5 ml of a 1% methanolic solution of p-toluenesulphonic acid are stirred at room temperature for one hour and then treated with 5% aqueous sodium hydrogen carbonate solution. After extracting by shaking three times with 20 ml of diethyl ether each time, drying over sodium sulphate, concentrating the organic phase and chromatographing the crude product on 20 g of silica gel (eluant: diethyl ether), 92 mg of 14,15-dichloromethylene-14,15-dihydromilbemycin $A_4$ are obtained; m.p. 127°–131° C.

By reacting 14,15-dichloromethylene-14,15-dihydromilbemycin $A_4$ with 2,3,4,6-tetraacetylglucopyranose, 5-O-(2,3,4 6-tetraacetylglucopyranosyl)-14,15-dichloromethylene- 14,15-dihydromilbemycin $A_4$, m.p. 133°–138° C. (compound no. 7.1) is obtained.

Example P-3: Preparation of
14,15-dichloromethylene-14,15-dihydromilbemycin $A_3$ With continuous stirring at from 0° to 3° C., 7 ml of a 50% aqueous sodium hydroxide solution are added to a solution of 400 mg (0.75 mmol) of milbemycin $A_3$ and 5 mg of tetrabutylammonium chloride in 50 ml of chloroform. After 15 minutes, the reaction mixture is diluted with 100 ml of diethyl ether and washed with water/sodium chloride solution until a neutral reaction is obtained. The solution is dried over sodium sulphate and concentrated by evaporation. The resulting residue is purified over a silica column (hexane:ether=4:1). Freeze-drying of the resulting product yields 212 mg of 14,15-dichloromethylene-14,15-dihydromilbemycin $A_3$; m.p. 130°–135° C.

Example P-1: Preparation of
14,15-dibromomethylene-14,15-dihydromilbemycin $A_4$ 0.5 ml of bromoform is added at room temperature to 100 mg of milbemycin $A_4$ and 100 mg of magnesium chippings in 5 ml of diethyl ether. The reaction mixture, in which an exothermic reaction commences after a few minutes, is maintained at from 30° to 35° C. by cooling with an ice bath until, after about one hour, the reaction is complete. The reaction mixture is filtered and concentrated. Purification of the crude product by column chromatography (silica gel; diethyl ether/hexane=10:1) yields 78 mg of 14,15-dibromomethylene-14,15-dihydromilbemycin $A_4$ which decomposes at 141°–144° C.

By introducing the —Si(CH$_3$)$_2$-tert.—C$_4$H$_9$ group into 14,15-dibromomethylene-14,15-dihydromilbemycin $A_4$, 5-O-(tert.-butyldimethylsilyl)-14,15-dibromomethylene-14,15-dihydromilbemycin $A_4$, m.p. 137°–141° C., is obtained.

Example P-5: Preparation of 5-O-(tert.-butyldimethyl-silyl)-14,15-dichloromethylene-14,15-dihydromilbemycin A4

1 ml of n-butyllithium is added dropwise at −60° C., under argon, to 100 mg of 5-O-(tert.-butyldimethylsilyl)milbemycin A4 in 4 ml of dry chloroform. The reaction mixture is slowly heated to 20° C., stirred thoroughly for 4 hours and then filtered and concentrated. The resulting crude product is purified by column chromatography (silica gel; diethyl ether/petroleum ether = 1:5). 90 mg of 5-O-(tert.-butyldimethylsilyl)-14,15-dichloromethylene-14,15-dihydromilbemycin A4, m.p. 103°–105° C., are obtained.

Example P-6: Preparation of 5-O-(tert.-butyldimethylsilyl)-14,15-monobromcmethylene-14,15-dihydromilbemycin A4 and 5-O-(tert.-butyldimethylsilyl)-14,15-methylene-14,15-dihydromilbemycin A4

2.0 g of zinc powder are slowly added at 15° C. to a solution of 200 mg (0.24 mmol) of 5-O-(tert.-butyl-dimethylsilyl)-14,15-dibromomethylene-14,15-dihydromilbemycin A4 in 10 ml of glacial acetic acid. After 4 hours, the solvent is evaporated off in vacuo and the residue is filtered and purified over a silica gel column (cyclohexane:ethyl acetate = 12:1). Freeze-drying yields 70 mg of 5-O-(tert.-butyldimethylsilyl)-14,15-monobromomethylene-14,15-dihydromilbemycin A4 in the form of an amorphous powder, m.p. 180°–185° C., and 100 mg of 5-O-(tert.-butyldimethylsilyl)-14,15-methylene-14,15-dihydromilbemycin A4 in amorphous form, which melts at approximately 75° C.

Example P-7: Preparation of 14,15-monobromomethylene-14,15-dihydromilbemycin A4

2 ml of 1% methanolic p-toluenesulphonic acid solution is added at room temperature to 70 mg of 5-O-(tert.-butyl-dimethylsilyl)-14,15-monobromomethylene-14,15-dihydromilbemycin A4. Working up in accordance with the foregoing Examples yields 14,15-monobromomethylene-14,15-dihydromilbemycin A4 in the form of an amorphous powder which melts at 85°–88° C.

Example P-8: Preparation of 14,15-methylene-14,15-dihydromilbemycin A4

2 ml of 1% methanolic p-toluenesulphonic acid solution is added at room temperature to 100 mg of 5-O-(tert.-butyldimethylsilyl)-14,15-methylene-14,15-dihydromilbemycin A4. Working up in accordance with the foregoing Examples yields 14,15-methylene-14,15-dihydromilbemycin A4 in the form of an amorphous powder which melts at 80°–83° C.

14,15-dichloromethylene-14,15-dihydromilbemycin A4 can be oxidised to 5-oxo-14,15-dichloromethylene-14,15-dihydromilbemycin A4 and, by reaction of this 5-oxo compound with hydroxylamine, it is possible to prepare 5-hydroxyimino-14,15-dichloro-14,15-dihydromilbemycin A4; m.p. 171°–173° C.

The following compounds of formula I, listed together with compounds of the preceding Examples, are also prepared analogously to the described procedures. This list does not, however, constitute any limitation.

TABLE 1

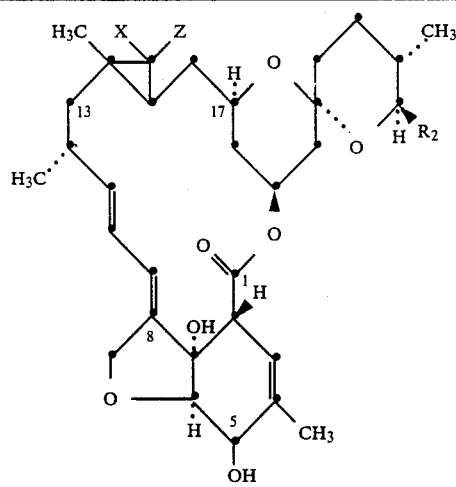

| Comp. No. | $R_2$ | X | Z |
|---|---|---|---|
| 1.1 | $CH_3$ | H | Br |
| 1.2 | $C_2H_5$ | H | Br |
| 1.3 | $C_3H_7$-iso | H | Br |
| 1.4 | $C_4H_9$-sec. | H | Br |
| 1.5 | $CH_3$ | H | Cl |
| 1.6 | $C_2H_5$ | H | Cl |
| 1.7 | $C_3H_7$-iso | H | Cl |
| 1.8 | $C_4H_9$-sec. | H | Cl |
| 1.9 | $CH_3$ | H | H |
| 1.10 | $C_2H_5$ | H | H |
| 1.11 | $C_3H_7$-iso | H | H |
| 1.12 | $C_4H_9$-sec. | H | H |
| 1.13 | $CH_3$ | Cl | Cl |
| 1.14 | $C_2H_5$ | Cl | Cl |
| 1.15 | $C_3H_7$-iso | Cl | Cl |
| 1.16 | $C_4H_9$-sec. | Cl | Cl |
| 1.17 | $CH_3$ | Br | Br |
| 1.18 | $C_2H_5$ | Br | Br |
| 1.19 | $C_3H_7$-iso | Br | Br |
| 1.20 | $C_4H_9$-sec. | Br | Br |
| 1.21 | $CH_3$ | H | F |
| 1.22 | $C_2H_5$ | I | I |
| 1.23 | $C_3H_7$-iso | Cl | Br |
| 1.24 | $C_4H_9$-sec. | H | I |
| 1.25 | $CH_3$ | Cl | Br |
| 1.26 | $C_2H_5$ | F | F |
| 1.27 | $C_3H_7$-iso | H | F |
| 1.28 | $C_4H_9$-sec. | Cl | I |
| 1.29 | $CH_3$ | F | F |
| 1.30 | $C_2H_5$ | Cl | Br |
| 1.31 | $C_3H_7$-iso | Br | F |
| 1.32 | $C_4H_9$-sec. | H | F |
| 1.33 | $CH_3$ | Br | I |
| 1.34 | $C_2H_5$ | H | F |
| 1.35 | $C_3H_7$-iso | F | F |
| 1.36 | $C_4H_9$-sec. | Cl | Br |
| 1.37 | $CH_3$ | F | I |
| 1.38 | $C_2H_5$ | H | I |
| 1.39 | $C_3H_7$-iso | Cl | I |
| 1.40 | $C_4H_9$-sec. | Br | F |
| 1.41 | $CH_3$ | H | I |
| 1.42 | $C_2H_5$ | Cl | F |
| 1.43 | $C_3H_7$-iso | Br | I |
| 1.44 | $C_4H_9$-sec. | I | I |
| 1.45 | $CH_3$ | Br | F |
| 1.46 | $C_2H_5$ | Cl | I |
| 1.47 | $C_3H_7$-iso | H | I |
| 1.48 | $C_4H_9$-sec. | F | F |
| 1.49 | $CH_3$ | Cl | I |
| 1.50 | $C_2H_5$ | Br | F |
| 1.51 | $C_3H_7$-iso | Cl | F |
| 1.52 | $C_4H_9$-sec. | Br | I |
| 1.53 | $CH_3$ | I | I |

TABLE 1-continued

| | | | |
|---|---|---|---|
| 1.54 | $C_2H_5$ | Br | F |
| 1.55 | $C_3H_7$-iso | F | I |
| 1.56 | $C_4H_9$-sec. | F | I |
| 1.57 | $CH_3$ | Cl | F |
| 1.58 | $C_2H_5$ | F | I |
| 1.59 | $C_3H_7$-iso | I | I |
| 1.60 | $C_4H_9$-sec. | Cl | F | and the compounds of Table 1 in which the hydrogen atom of the hydroxy group in the 5-position has been replaced by the silyl group —Si($CH_3$)$_2$-tert.—$C_4H_9$ (=compounds S—1.1 to S 1.60) and the compounds of Table 1 in which the hydrogen atom of the hydroxy group in the 5-position has been replaced by the acyl group —$COCH_3$ (=compounds A-1.1 to A-1.60).

TABLE 2-continued

| | | | | | |
|---|---|---|---|---|---|
| 2.36 | $CH_3$ | Cl | F | Cl | Br |
| 2.37 | $C_2H_5$ | F | I | H | H | and the compounds of Table 2 in which the hydrogen atom of the hydroxy group in the 5-position has been replaced by the silyl group —Si($CH_3$)$_2$—tert.—$C_4H_9$ )=compounds S-2.1 to S-2.37) and the compounds of Table 2 in which the hydrogen atom of the hydroxy group in the 5-position has been replaced by the acyl group —$COCH_3$ (=compounds A-2.1 to A-2.37).

TABLE 2

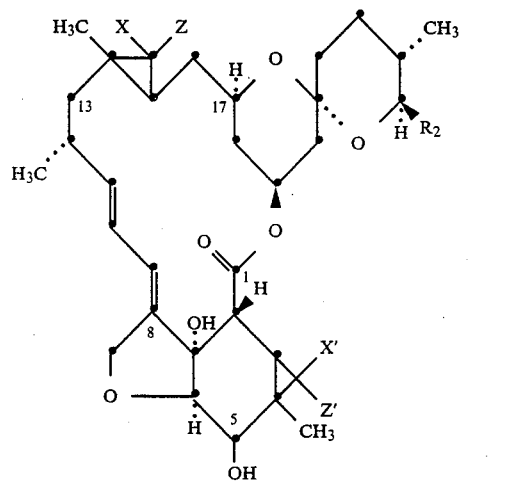

| Comp. No. | $R_2$ | X | Z | X' | Z' |
|---|---|---|---|---|---|
| 2.1 | $CH_3$ | H | Br | H | Br |
| 2.2 | $C_2H_5$ | H | Br | H | Br |
| 2.3 | $C_3H_7$-iso | H | Br | H | Cl |
| 2.4 | $C_4H_9$-sec. | H | Br | H | Cl |
| 2.5 | $CH_3$ | H | Cl | H | H |
| 2.6 | $C_2H_5$ | H | Cl | H | Cl |
| 2.7 | $C_3H_7$-iso | H | Cl | H | H |
| 2.8 | $C_4H_9$-sec. | H | Cl | H | Br |
| 2.9 | $CH_3$ | H | H | H | H |
| 2.10 | $C_2H_5$ | H | H | Cl | Cl |
| 2.11 | $C_3H_7$-iso | H | H | Br | Br |
| 2.12 | $C_4H_9$-sec. | H | H | H | H |
| 2.13 | $CH_3$ | Cl | Cl | Cl | Cl |
| 2.14 | $C_2H_5$ | Cl | Cl | Cl | Cl |
| 2.15 | $C_3H_7$-iso | Cl | Cl | Br | Br |
| 2.16 | $C_4H_9$-sec. | Cl | Cl | I | I |
| 2.17 | $CH_3$ | Br | Br | H | H |
| 2.18 | $C_2H_5$ | Br | Br | Br | Br |
| 2.19 | $C_3H_7$-iso | Br | Br | Br | Br |
| 2.20 | $C_4H_9$-sec. | Br | Br | H | H |
| 2.21 | $CH_3$ | H | F | H | F |
| 2.22 | $C_2H_5$ | I | I | I | I |
| 2.23 | $C_3H_7$-iso | Cl | Br | Cl | Cl |
| 2.24 | $CH_3$ | Cl | Br | Cl | Br |
| 2.25 | $C_2H_5$ | F | F | F | F |
| 2.26 | $CH_3$ | F | F | Cl | Cl |
| 2.27 | $C_2H_5$ | Cl | Br | Cl | Br |
| 2.28 | $C_4H_9$-sec. | H | F | H | H |
| 2.29 | $C_2H_5$ | H | F | H | F |
| 2.30 | $C_3H_7$-iso | F | F | F | F |
| 2.31 | $C_4H_9$-sec. | Cl | Br | Cl | Cl |
| 2.32 | $C_2H_5$ | H | I | H | Cl |
| 2.33 | $CH_3$ | H | I | H | I |
| 2.34 | $C_2H_5$ | Cl | F | Cl | F |
| 2.35 | $CH_3$ | I | I | Cl | Cl |

TABLE 3

| Comp. No | $R_2$ | X | Z |
|---|---|---|---|
| 3.1 | $CH_3$ | H | H |
| 3.2 | $C_2H_5$ | H | H |
| 3.3 | $C_3H_7$-iso | H | H |
| 3.4 | $C_4H_9$-sec. | H | H |
| 3.5 | $CH_3$ | Br | Br |
| 3.6 | $C_2H_5$ | Br | Br |
| 3.7 | $C_3H_7$-iso | Br | Br |
| 3.8 | $C_4H_9$-sec. | Br | Br |
| 3.9 | $CH_3$ | Cl | Cl |
| 3.10 | $C_2H_5$ | Cl | Cl |
| 3.11 | $C_3H_7$-iso | Cl | Cl |
| 3.12 | $C_4H_9$-sec. | Cl | Cl |
| 3.13 | $CH_3$ | H | Br |
| 3.14 | $C_2H_5$ | H | Br |
| 3.15 | $C_3H_7$-iso | H | Br |
| 3.16 | $C_4H_9$-sec. | H | Br |
| 3.17 | $CH_3$ | H | Cl |
| 3.18 | $C_2H_5$ | H | Cl |
| 3.19 | $C_3H_7$-iso | H | Cl |
| 3.20 | $C_4H_9$-sec. | H | Cl |
| 3.21 | $CH_3$ | H | F |
| 3.22 | $C_2H_5$ | H | F |
| 3.23 | $C_3H_7$-iso | H | F |
| 3.24 | $C_4H_9$-sec. | H | F |

TABLE 4

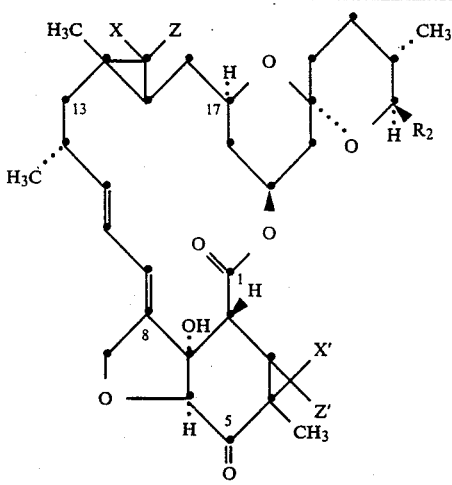

| Comp. No. | $R_2$ | X | Z | X' | Z' |
|---|---|---|---|---|---|
| 4.1 | $C_3H_7$-iso | Cl | Cl | Br | Br |
| 4.2 | $CH_3$ | Br | Br | Cl | Cl |
| 4.3 | $C_2H_5$ | H | Br | H | Br |
| 4.4 | $CH_3$ | H | H | H | H |
| 4.5 | $C_4H_9$-sec. | Br | Br | H | H |
| 4.6 | $CH_3$ | H | Br | H | Cl |
| 4.7 | $C_3H_7$-iso | H | H | H | H |
| 4.8 | $C_2H_5$ | Cl | Cl | Cl | Cl |
| 4.9 | $C_4H_9$-sec. | Cl | Cl | H | H |
| 4.10 | $C_2H_5$ | H | H | Cl | Cl |
| 4.11 | $C_2H_5$ | Br | Br | Br | Br |
| 4.12 | $CH_3$ | Cl | Cl | Cl | Cl |

TABLE 5

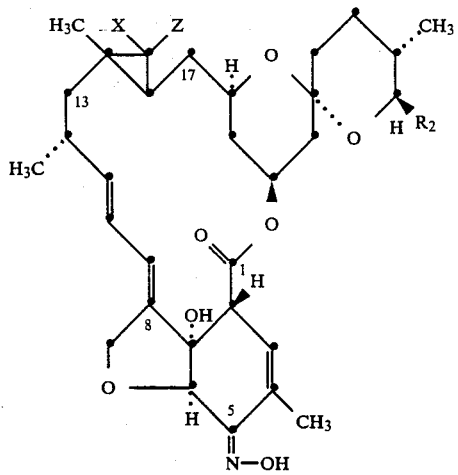

| Comp. No. | $R_2$ | X | Z |
|---|---|---|---|
| 5.1 | $CH_3$ | H | H |
| 5.2 | $C_2H_5$ | H | H |
| 5.3 | $C_3H_7$-iso | H | H |
| 5.4 | $C_4H_9$-sec. | H | H |
| 5.5 | $CH_3$ | Br | Br |
| 5.6 | $C_2H_5$ | Br | Br |
| 5.7 | $C_3H_7$-iso | Br | Br |
| 5.8 | $C_4H_9$-sec. | Br | Br |
| 5.9 | $CH_3$ | Cl | Cl |
| 5.10 | $C_2H_5$ | Cl | Cl |
| 5.11 | $C_3H_7$-iso | Cl | Cl |
| 5.12 | $C_4H_9$-sec. | Cl | Cl |
| 5.13 | $CH_3$ | H | Br |

TABLE 5-continued

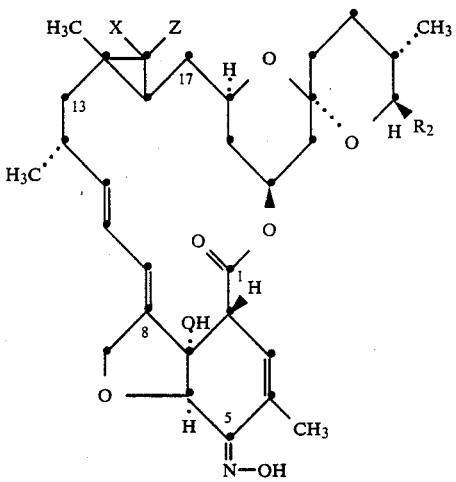

| Comp. No. | $R_2$ | X | Z |
|---|---|---|---|
| 5.14 | $C_2H_5$ | H | Br |
| 5.15 | $C_3H_7$-iso | H | Br |
| 5.16 | $C_4H_9$-sec. | H | Br |
| 5.17 | $CH_3$ | H | Cl |
| 5.18 | $C_2H_5$ | H | Cl |
| 5.19 | $C_3H_7$-iso | H | Cl |
| 5.20 | $C_4H_9$-sec. | H | Cl |
| 5.21 | $CH_3$ | H | F |
| 5.22 | $C_2H_5$ | H | F |
| 5.23 | $C_3H_7$-iso | H | F |
| 5.24 | $C_4H_9$-sec. | H | F | and the compounds of Table 5 in which the hydrogen atom of the oxime group in the 5-position has been replaced by the silyl group $-Si(CH_3)_2$-tert.$-C_4H_9$ (=compounds S-5.1 to S-5.24) and the compounds of Table 5 in which the hydrogen atom of the oxime group in the 5-position has been replaced by the acyl group $-COCH_3$ (=compounds A-5.1 to A-5.24).

TABLE 6

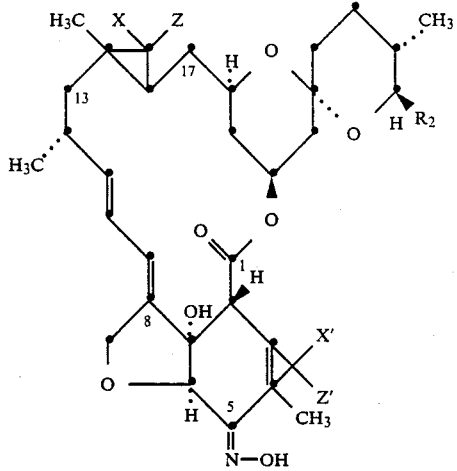

| Comp. No. | $R_2$ | X | Z | X' | Z' |
|---|---|---|---|---|---|
| 6.1 | $CH_3$ | Cl | Cl | Cl | Cl |
| 6.2 | $C_2H_5$ | Br | Br | Br | Br |
| 6.3 | $C_2H_5$ | H | H | H | H |
| 6.4 | $C_4H_9$-sec. | Cl | Cl | H | H |
| 6.5 | $C_2H_5$ | Cl | Cl | Cl | Cl |

TABLE 6-continued

| | | | | | | |
|---|---|---|---|---|---|---|
| 6.6 | C$_3$H$_7$-iso | H | H | Br | Br |
| 6.7 | CH$_3$ | H | Br | H | Br |
| 6.8 | C$_4$H$_9$-sec. | Br | Br | Cl | Cl |
| 6.9 | CH$_3$ | H | H | H | Cl |
| 6.10 | C$_2$H$_5$ | H | Br | H | Br |
| 6.11 | CH$_3$ | Br | Br | H | H |
| 6.12 | C$_3$H$_7$-iso | Cl | Cl | Br | Br |
| 6.13 | C$_2$H$_5$ | Cl | Br | Br | Cl |
| 6.14 | C$_4$H$_9$-sec. | Br | Cl | Br | Cl | and the compounds of Table 6 in which the hydrogen atom of the oxime group in the 5-position has been replaced by the silyl group —Si(CH$_3$)$_2$—tert.—C$_4$H$_9$ (=compounds S-6.1 to S-6.14 and the compounds of Table 6 in which the hydrogen atom of the oxime group in the 5-position has been replaced by the acyl group —COCH$_3$ (=compounds A-6.1 to A-6.14).

Formulation Examples for the active ingredient of formula I
(% = percent by weight)

| Wettable powders | (a) | (b) | (c) |
|---|---|---|---|
| an active ingredient from Tables 1 to 6 | 25% | 50% | 75% |
| sodium lignosulphonate | 5% | 5% | — |
| sodium laurylsulphate | 3% | — | 5% |
| sodium diisobutylnaph-thalenesulphonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill. Wettable powders are obtained which can be diluted with water to give suspensions of any desired concentration.

| Emulsifiable concentrate | |
|---|---|
| an active ingredient from Tables 1 to 6 | 10% |
| octylphenol polyethylene glycol ether (4–5 moles of ethylene oxide) | 3% |
| calcium dodecylbenzene-sulphonate | 3% |
| castor oil polyglycol ether (36 moles of ethylene oxide) | 4% |
| cyclohexanone | 30% |
| xylene mixture | 50% |

Emulsions of any desired concentration can be prepared from this concentrate by dilution with water.

| Dusts | (a) | (b) |
|---|---|---|
| an active ingredient from Tables 1 to 6 | 5% | 8% |
| talcum | 95% | — |
| kaolin | — | 92% |

Ready-for-use dusts are obtained by mixing the active ingredient with the carrier and grinding the mixture in a suitable mill.

| Extruder granulate | |
|---|---|
| an active ingredient from Tables 1 to 6 | 10% |
| sodium lignosulphonate | 2% |
| carboxymethylcellulose | 1% |
| kaolin | 87% |

The active ingredient is mixed and ground with the adjuvants, and the mixture is moistened with water. This mixture is extruded and then dried in a stream of air.

| Tablets or boli | | |
|---|---|---|
| I | an active ingredient from Tables 1 to 6 | 33.00% |
| | methylcellulose | 0.80% |
| | highly dispersed silicic acid | 0.80% |
| | maize starch | 8.40% |

The methylcellulose is stirred in water and allowed to swell; silicic acid is stirred in to give a homogeneous suspension. The active ingredient and the maize starch are mixed and the aqueous suspension is incorporated into this mixture, which is kneaded to a paste. This mass is granulated through a sieve (mesh width 12M) and the granulate is then dried.

| | | |
|---|---|---|
| II | crystalline lactose | 22.50% |
| | maize starch | 17.00% |
| | microcrystalline cellulose | 16.50% |
| | magnesium stearate | 1.00% |

All 4 adjuvants are thoroughly mixed.

Phases I and II are mixed and compressed to form tablets or boli.

| Injectable composition A. Oily vehicle (slow release) | |
|---|---|
| an active ingredient from the Tables | 0.1–1.0 g |
| groundnut oil | ad 100 ml |
| an active ingredient from the Tables | 0.1–1.0 g |
| sesame oil | ad 100 ml |

Preparation: The active ingredient is dissolved in some of the oil while stirring and, if necessary, while heating gently; after cooling, the solution is made up to the prescribed volume and sterile-filtered through a suitable membrane filter having a pore diameter of 0.22 μm.

| B. Water-miscible solvent (medium rate of release) | |
|---|---|
| an active ingredient from the Tables | 0.1–1.0 g |
| 4-hydroxymethyl-1,3-dioxolane (glycerol formal) | 40.0 g |
| 1,2-propanediol | ad 100 ml |
| an active ingredient from the Tables | 0.1–1.0 g |
| glycerin dimethyl ketal | 40.0 g |
| 1,2-propanediol | ad 100 ml |

Preparation: the active ingredient is dissolved in some of the solvent while stirring, and the solution is made up to the prescribed volume and sterile-filtered through a suitable membrane filter having a pore diameter of 0.22 μm.

| C. Aqueous solubilisate (rapid release) | |
|---|---|
| an active ingredient from the Tables | 0.1–1.0 g |
| polyethoxylated castor oil (40 ethylene oxide units)* | 10 g |
| 1,2-propanediol | 20 g |
| benzyl alcohol | 1 g |
| aqua ad inject. | ad 100 ml |
| an active ingredient from the Tables | 0.1–1.0 g |
| polyethoxylated sorbitan monooleate (20 ethylene oxide units)** | 8 g |
| 4-hydroxymethyl-1,3-dioxolane (glycerol formal) | 20 g |
| benzyl alcohol | 1 g |
| aqua ad inject. | ad 100 ml |

*Available commercially under the name CREMOPHOR ® EL (BASF AG);
**Available commercially under the name TWEEN ® 80 (ICI);

Preparation: the active ingredient is dissolved in the solvents and the surfactant and the solution is made up to the prescribed volume with water. Sterile-filtration is carried out through a suitable membrane filter having a pore diameter of 0.22 μm.

The aqueous systems can preferably also be used for oral and/or intraruminal administration.

When compounds of formula I or corresponding compositions are used for controlling endoparasitic nematodes, cestodes and trematodes in domestic animals and productive livestock, such as cattle, sheep, goats, cats and dogs, the compounds or compositions can be administered to the animal either as a single dose or repeatedly, the individual doses preferably being from 0.1 to 10 mg per kg of body weight depending on the type of animal. By protracted administration it is possible in some cases to achieve a better action or lower overall doses can suffice. The active ingredient, or the composition containing it, can also be added to the feed or the drink. The concentration of active ingredient in the prepared feed is preferably from 0.005 to 0.1% by weight. The compositions can be administered to the animals perorally in the form of solutions, emulsions, suspensions, powders, tablets, boli or capsules. Provided that the physical and toxicological properties of solutions or emulsions permit, the compounds of formula I, or the compositions containing them, can also be administered to the animal, for example, by subcutaneous injection or intraruminally, or can be applied to the body of the animal by means of the pour-on method. It is also possible to administer the active ingredient to the animal by means of licks (salt) or molasses blocks.

Biological Examples

B-1 Action against $L_1$ larvae of Lucilia sericata 1 ml of an aqueous suspension of the active substance to be tested is mixed in such a manner with 3 ml of a special larval culture medium at about 50° C. that a homogeneous composition containing, as desired, 250 ppm or 125 ppm of active ingredient is obtained. About 30 Lucilia larvae ($L_1$) are put into each test tube containing active ingredient. The mortality rate is ascertained after 4 days. Compounds from the Preparation Examples, such as, for example, compounds Nos. 1.14, 1.18, 5.5 and 7.1 (compound from Example P-2), achieve 100% effectiveness at 100 ppm.

These results are also obtained in the same test against $L_1$ larvae of Lucilia cuprina.

B-2: Acaricidal action against Boophilus microplus (Biarra strain)

Adhesive tape is so applied horizontally across a PVC plate that 10 female Boophilus microplus ticks (Biarra strain) fully replete with blood can be affixed thereto on their backs, side by side, in a row. Each tick is injected from an injection needle with 1 μl of a liquid which is a 1:1 mixture of polyethylene glycol and acetone, in which mixture a specific amount of active ingredient of, as desired, 1, 0.1 or 0.01 μl per tick is dissolved. Control ticks are injected with a corresponding mixture that does not contain the active ingredient. After this treatment, the ticks are kept in an insectarium under normal conditions at about 28° C. and 80% relative humidity until oviposition has taken place and the larvae have emerged from the eggs of the control ticks.

The activity of a tested substance is determined by the $IR_{90}$, i.e. that dose of active ingredient is determined at which 9 out of 10 female ticks (90%), even after 30 days, lay eggs from which larvae are unable to emerge. Compounds from the Preparation Examples achieve an $IR_{90}$ of 1 μg.

B-3: Trial with sheep infected with nematodes (Haemonchus contortus and Trichostrongylus colubriformis The active ingredient is formulated as a suspension and administered using a stomach probe or by intraruminal injection to sheep that have been artificially infected with Haemonchus contortus and Trichostrongylus colubriformis. 1 to 3 animals are used for each dose. Each sheep is treated only once with a single dose of, as desired, 0.5 mg or 0.1 mg/kg of body weight. Evaluation is made by comparing the number of worm eggs excreted in the faeces of the sheep before and after treatment.

Sheep infected simultaneously and in the same manner but untreated are used as controls. In comparison with untreated but infected control groups, nematode infestation was reduced by from 50 to 100% (=reduction of worm eggs in the faeces) in sheep that had been treated with 0.1 mg/kg of one of the compounds from the Preparation Examples, such as, for example, No. 1.14, 1.18, 2.14 or 5.5.

B-4: Larvicidal action against Aedes aegypti

A 0.1% solution of the active ingredient in acetone is pipetted onto the surface of 150 ml of water in containers in amounts sufficient to give concentrations of, as desired, 10 ppm, 3.3 ppm and 1.6 ppm. After the acetone has evaporated, about 30 to 40 three-day-old Aedes larvae are put into each container. Mortality counts are made after 1, 2 and 5 days.

In this test, compounds from Tables 1 to 6 at a concentration of 10 ppm achieve complete kill of all larvae after only 1 day.

B-5: Miticidal action against Dermanyssus gallinae 2 to 3 ml of a test solution (100, 10, 1 and 0.1 ppm of active substance) are put into a glass container which is open at the top and about 200 mites in different stages of development are put into this container. The glass container is sealed with a wad of cotton wool and is uniformly shaken for 10 minutes until the mites are completely wet. The container is then inverted until excess test solution has been absorbed by the cotton wool. The container is then stood upright again and the treated mites are kept under observation for 3 days under laboratory conditions to evaluate the effectiveness of the test substances. Mortality is the criterion for effectiveness.

Compounds from the Preparation Examples, such as, for example, Nos. 1.14, 1.18 and 5.5, exhibit 100% effectiveness at 100 ppm.

I claim:

1. A compound of formula I

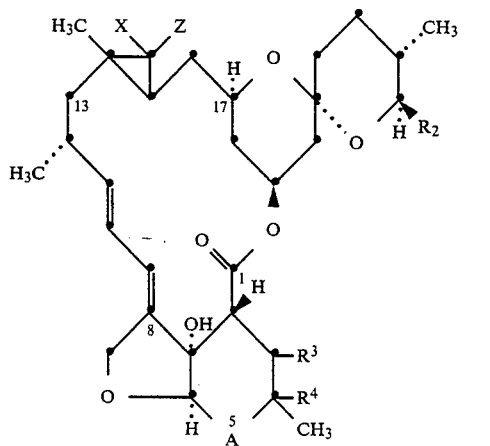

(I)

in which

A is a $$-\underset{OR_1}{\overset{|}{CH}}-,\ -\underset{O}{\overset{\|}{C}}-\ \text{or}\ -\underset{N-OR_{11}}{\overset{\|}{C}}-$$

group wherein $R_1$ is hydrogen, $R_5$—C(O), $Si(R_6)(R_7)(R_8)$ or 2,3,4,6-tetraacetyllglucopyranosyl;

$R_5$ is $C_1$-$C_{10}$-alkyl, $C_1$-$C_{10}$-haloalkyl, a phenyl or a benzyl, which is unsubstituted or its substituted by at least one substituent selected from the group consisting of halogen, $C_1$-$C_3$-alkyl, $C_1$-$C_3$-haloalkyl, $C_1$-$C_3$-alkoxy, $C_1$-$C_3$-haloalkoxy, cyano and nitro;

$R_6$, $R_7$ and $R_8$ independently of each other are $C_1$-$C_4$-alkyl, benzyl or phenyl; $R_{11}$ is hydrogen, $R_5$C(O)-$Si(R_6)(R_7)(R_8)$ $C_1$-$C_8$-alkyl or $C_3$-$C_6$-cycloalkyl; $R_2$ is methyl, ethyl isopropyl, sec.-butyl or a —C(CH$_3$)=CH—E group wherein E is methyl, ethyl or isopropyl;

$R_3$ and $R_4$ together represent a bond between the two carbon atoms to which they are bound, or together represent a —C(X')(Z')— group wherein Z' and Z' each represents, independently of the other, hydrogen or halogen; and X and Z each represents, independently of the other, hydrogen or halogen.

2. A compound of formula I according to claim 1, wherein A, $R_3$, $R_4$, X and Z are as defined for formula I, and $R_2$ is methyl, ethyl, isopropyl or sec.-butyl.

3. A compound of formula I according to claim 2, wherein A is any one of the groups —CH(OR$_1$)—, —C(O)— or—C(=N—OH)— wherein $R_1$ is hydrogen $Si(R_6)(R_7)(R_8)$ or 2,3,4,6-tetrahydroglucopyranosyl, and $R_2$ is methyl or ethyl.

4. A compound of formula I according to claim 2, wherein A is any one of the groups —CH(OR$_1$)—, —C(O)— or —C(=N—OH)— wherein $R_1$ is hydrogen, acetyl, tert.-butyldimethylsilyl or 2,3,4,6-tetraacetylglucopyranosyl $R_2$ is methyl or ethyl, $R_3$ and $R_4$ together form a bond between the two carbon atoms to which they are bound, or together form a —C(Cl$_2$)— group, X is hydrogen, chlorine, bromine or fluorine, and Z is hydrogen, chlorine, bromine or fluorine.

5. A compound of formula I according to claim 2, wherein A is any one of the groups —CH(OR$_1$)—, —C(O)— or —C(=N—OH)— wherein $R_1$ is hydrogen, tert.-butyldimethylsilyl or 2,3,4,6-tetraacetylglucopyranosyl, $R_2$ is methyl or ethyl, $R_3$ and $R_4$ together form a bond between the two carbon atoms to which they are bound, or together form a —C(Cl$_2$)— group, X is hydrogen, chlorine or bromine, and Z is hydrogen, chlorine or bromine.

6. A compound of formula I according to claim 2, wherein A is a —CH(OH)— or —C(=N—OH)— group, $R_2$ is methyl or ethyl, $R_3$ and $R_4$ together form a bond between the two carbon atoms to which they are bound, X is hydrogen, chlorine, bromine or fluorine, and Z is hydrogen, chlorine, bromine or fluorine.

7. A compound of formula I according to claim 2, wherein A is a —CH(OH)— or —C(=N—OH)— group, $R_2$ is methyl or ethyl, $R_3$ and $R_4$ together form a bond between the two carbon atoms to which they are bound, and X and Z are identical with each other and each represents hydrogen, chlorine or bromine, or X is hydrogen and Z is chlorine or bromine.

8. A compound of formula I according to claim 2, wherein A is a —CH(OH)— group, $R_2$ is methyl or ethyl, $R_3$ and $R_4$ together form a bond between the two carbon atoms to which they are bound, or together form a —CCl$_2$— group, X is hydrogen, chlorine or bromine, and Z is hydrogen, chlorine or bromine.

9. A compound of formula I according to claim 2, selected from the group consisting of:

5-O-(tert.-butyldimethylsilyl)-14,15-dichloromethylene-14,15-dihydromilbemycin A$_4$, 5-O-(tert.-butyldimethylsilyl)-3,4-dichloromethylene-14,15-dichloromethylene-3,4,14,15-tetrahydromilbemycin A$_4$, 3,4-dichloromethylene-14,15-dichloromethylene-3,4,14,15-tetrahydromilbemycin A$_4$, 5-O-(tert.-butyldimethylsilyl)-14,15-dibromomethylene-14,15-dihydromilbemycin A$_4$, 5-O-(2,3,4,6-tetraacetylglucopyranosyl)-14,15-dichloro-methylene-14,15-dihydromilbemycin $A_4$,
5-oxo-14,15-dichloromethylene-14,15-dihydromilbemycin $A_4$,
5-hydroxyimino-14,15-dichloromethylene-14,15-dihydromilbemycin $A_4$,
14,15-dichloromethylene-14,15-dihydromilbemycin $A_3$,
5-O-(tert.-butyldimethylsilyl)-14,15-monobromomethylene-14,15-dihydromilbemycin $A_4$,
14,15-monobromomethylene-14,15-dihydromilbemycin $A_4$,
4,15-monochloromethylene-14,15-dihydromilbemycin $A_4$,
5-O-tert.-butyldimethylsilyl)-14,15-methylene-14,15-dihydromilbemycin $A_4$,
14,15-methylene-14,15-dihydromilbemycin $A_4$,
14,15-dibromomethylene-14,15-dihydromilbemycin $A_4$ and
14,15-dichloromethylene-14,15-dihydromilbemycin $A_4$.

10. A composition for controlling ecto- and endoparasites in productive livestock or for controlling harmful insects, characterized in that it contains, as active ingredient, at least one compound of formula I according to claim 1, together with a carriers.

11. A composition according to claim 10, characterized in that it contains, as active ingredient, a compound of formula I wherein A, $R_3$, $R_4$, X and Z are as defined for formula I, and $R_2$ is methyl, ethyl, isopropyl or sec.-butyl.

12. A method of controlling parasites or harmful insects that infest productive livestock, characterized in that a parasiticidally or insecticidally effective amount of at least one compound of formula I according to claim 1 is applied to the parasite, the harmful insect or to the environment thereof.

13. A method according to claim 12, characterized in that a compound of formula I wherein A, $R_3$, $R_4$, X and Z are as defined for formula I, and $R_2$ is methyl, ethyl, isopropyl or sec.-butyl, is applied.

* * * * *